(12) United States Patent
Divi et al.

(10) Patent No.: US 8,569,483 B2
(45) Date of Patent: Oct. 29, 2013

(54) PROCESS FOR THE PREPARATION OF BAZEDOXIFENE ACETATE AND INTERMEDIATES THEREOF

(75) Inventors: Murali Krishna Prasad Divi, Hyderabad (IN); Gundu Rao Padakandla, Hyderabad (IN); Bolneni Nageswara Rao, Hyderabad (IN); Dandu Venkata Suresh, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 186 days.

(21) Appl. No.: 13/227,898

(22) Filed: Sep. 8, 2011

(65) Prior Publication Data

US 2012/0330008 A1    Dec. 27, 2012

(30) Foreign Application Priority Data

Jun. 21, 2011  (IN) .............. 2101/CHE/2011

(51) Int. Cl.
*C07D 403/00*    (2006.01)

(52) U.S. Cl.
USPC ........................................ 540/602

(58) Field of Classification Search
USPC ........................................ 540/602
See application file for complete search history.

(56) References Cited

U.S. PATENT DOCUMENTS

| | | | |
|---|---|---|---|
| 5,998,402 | A | 12/1999 | Miller et al. |
| 6,380,166 | B1 | 4/2002 | Miller et al. |

FOREIGN PATENT DOCUMENTS

| | | |
|---|---|---|
| EP | 0802183 A1 | 10/1997 |
| WO | 9919293 A1 | 4/1999 |
| WO | 2010118997 A1 | 10/2010 |
| WO | 2011022596 A2 | 2/2011 |

OTHER PUBLICATIONS

Chris P. Miller, et al. Design, Synthesis and Preclinical Characterization of Novel, Highly Selective Indole Estrogens, Wyeth-Ayerst Research, Chemical Sciences, J. Med. Chem. 44 (11), pp. 1654-1657, 2001.

*Primary Examiner* — Brenda Coleman

(74) *Attorney, Agent, or Firm* — Caesar, Rivise, Bernstein, Cohen & Pokotilow, Ltd.

(57) ABSTRACT

A novel process is described for the preparation of pharmaceutically useful compounds such as 1-{4-[2-(azepan-1-yl)ethoxy]benzyl}-2-(4-hydroxyphenyl)-3-methyl-1H-indol-5-ol acetic acid commonly known as bazedoxifene acetate of the formula-1 using 2-(4-{[5-(benzyloxy)-2-[4-(benzyloxy)phenyl]-3-methyl-1H-indol-1-yl]methyl}phenoxy)ethyl-4-methylbenzenzene-1-sulfonate (formula 2a)

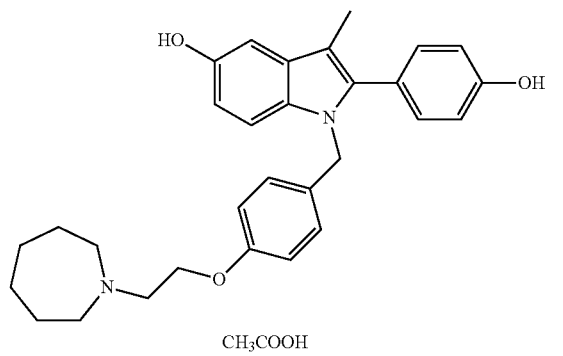

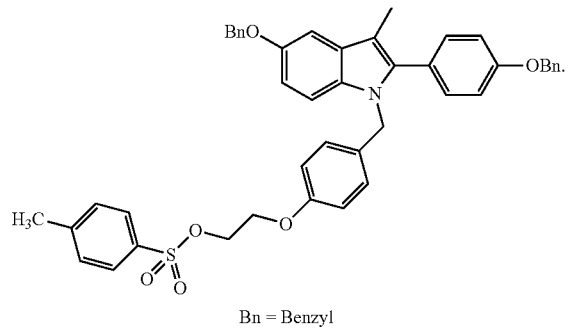

Bn = Benzyl

5 Claims, No Drawings

PROCESS FOR THE PREPARATION OF BAZEDOXIFENE ACETATE AND INTERMEDIATES THEREOF

CROSS-REFERENCE TO RELATED APPLICATION

This application claims priority from India Application 2101/CHE/2011, filed Jun. 21, 2011, entitled A NOVEL PROCESS FOR THE PREPARATION OF BAZEDOXIFENE ACETATE AND INTERMEDIATES THEREOF, which application is assigned to the same assignee as this application and whose disclosure is incorporated by reference herein.

FIELD OF INVENTION

The present invention relates to a novel process for preparing 1-{4-[2-(azepan-1-yl)ethoxy]benzyl}-2-(4-hydroxyphenyl)-3-methyl-1H-indol-5-ol and its acetate, also known as bazedoxifene acetate from 2-(4-{[5-(benzyloxy)-2-[4-(benzyloxy)phenyl]-3-methyl-1H-indol-1-yl]methyl}phenoxy)ethyl-4-methylbenzenzene-1-sulfonate (formula 2a).

BACKGROUND ART

Bazedoxifene acetate 1-{4-[2-(azepan-1-yl)ethoxy]benzyl}-2-(4-hydroxyphenyl)-3-methyl-1H-indol-5-ol acetate is a third generation selective estrogen receptor modulator. It is used in the prevention and treatment of post menopausal osteoporosis.

Conventional processes for preparing bazedoxifene acetate are disclosed in U.S. Pat. Nos. 5,998,402, 6,380,166, European patent 0802183 and World patent application 2010118997. Miller et al., (*J. Med. Chem.*, 2001, 44, 1654-57) have also described a synthetic preparation of bazedoxifene acetate.

Scheme 1 below summarizes the method disclosed in U.S. Pat. No. 5,998,402, EP 0802183 and in *J. Med. Chem.* 2001, 44, 1654-57.

Alkylation of the indole of the formula-3 with the compound of formula-4 was accomplished with sodium hydride in N,N-dimethyl formamide. The ester of formula-5 was subsequently reduced with lithium aluminium hydride (LAH) and the primary alcohol of formula-6 thus produced was converted to the corresponding bromide of formula-7 by treatment with carbontetrabromide and triphenylphosphine. Substitution of this bromide of formula-7 with hexamethyleneimine yielded benzylated bazedoxifene of formula-8. Hydrogenation of the compound of formula-8 to bazedoxifene free base of formula-9 was followed by conversion to bazedoxifene acetate of the formula-1.

The drawbacks of this process involve using LAH, a highly flammable and industrially hazardous reagent, and using $CBr_4$ a corrosive and expensive Class 1 solvent and reagent at the bromination stage.

Scheme-1:

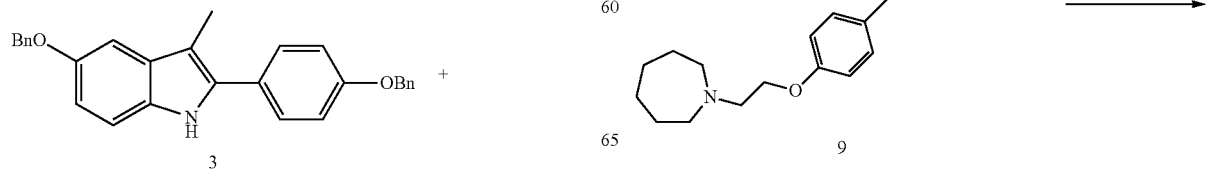

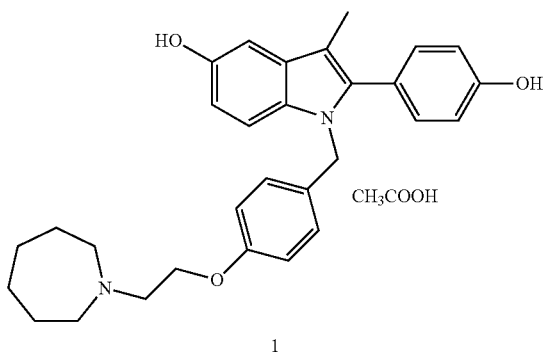

A second method is disclosed in U.S. Pat. No. 6,380,166 and WO 9919293 (Shown as Scheme 2). Alkylation of indole with the compound of formula-10 was accomplished with sodium-tert-butoxide in N,N-dimethyl formamide yielding benzylated bazedoxifene directly. The remaining steps are similar to the Scheme I above.

The WO 2011022596A2 application discloses a process similar to the one described in U.S. Pat. No. 6,380,166, wherein the alkylation of indole with the compound of formula-10 was prepared by using sodium hydride in DMF to yield the benzylated bazedoxifene of formula-8 along with C-alkylated impurity of formula-23. This impurity subsequently undergoes reaction to give debenzylated impurity of formula-22. The impure free base was further converted to bazedoxifene hydrochloride in methanol by treating with aqueous hydrochloric acid. However, the described process resulted in a yield loss of 20 to 25%.

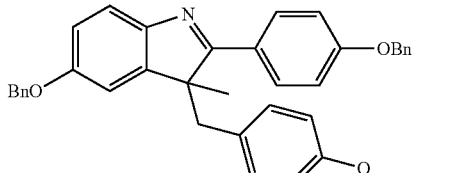

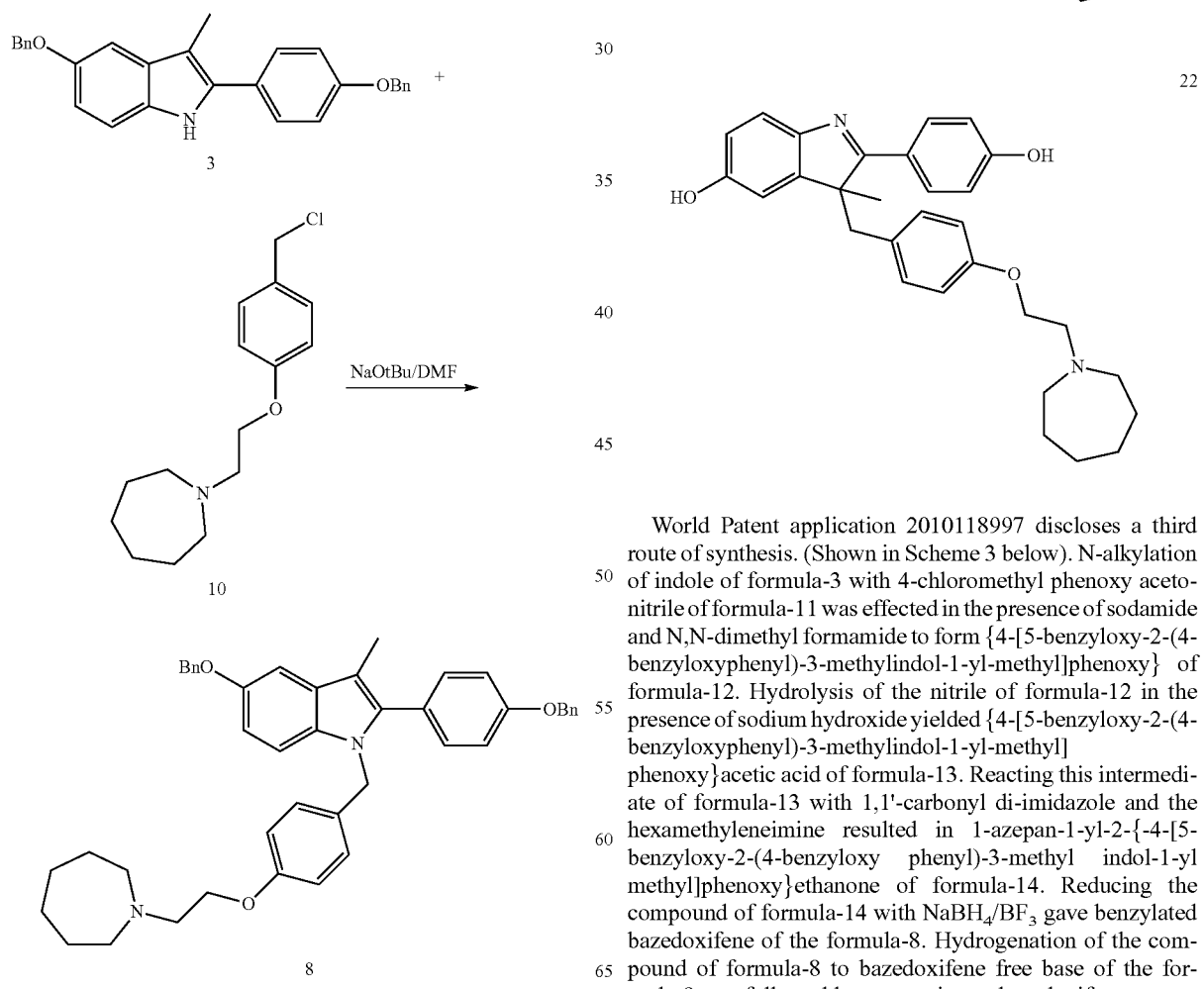

World Patent application 2010118997 discloses a third route of synthesis. (Shown in Scheme 3 below). N-alkylation of indole of formula-3 with 4-chloromethyl phenoxy acetonitrile of formula-11 was effected in the presence of sodamide and N,N-dimethyl formamide to form {4-[5-benzyloxy-2-(4-benzyloxyphenyl)-3-methylindol-1-yl-methyl]phenoxy} of formula-12. Hydrolysis of the nitrile of formula-12 in the presence of sodium hydroxide yielded {4-[5-benzyloxy-2-(4-benzyloxyphenyl)-3-methylindol-1-yl-methyl] phenoxy}acetic acid of formula-13. Reacting this intermediate of formula-13 with 1,1'-carbonyl di-imidazole and the hexamethyleneimine resulted in 1-azepan-1-yl-2-{-4-[5-benzyloxy-2-(4-benzyloxy phenyl)-3-methyl indol-1-yl methyl]phenoxy}ethanone of formula-14. Reducing the compound of formula-14 with $NaBH_4/BF_3$ gave benzylated bazedoxifene of the formula-8. Hydrogenation of the compound of formula-8 to bazedoxifene free base of the formula-9 was followed by conversion to bazedoxifene acetate of the formula-1.

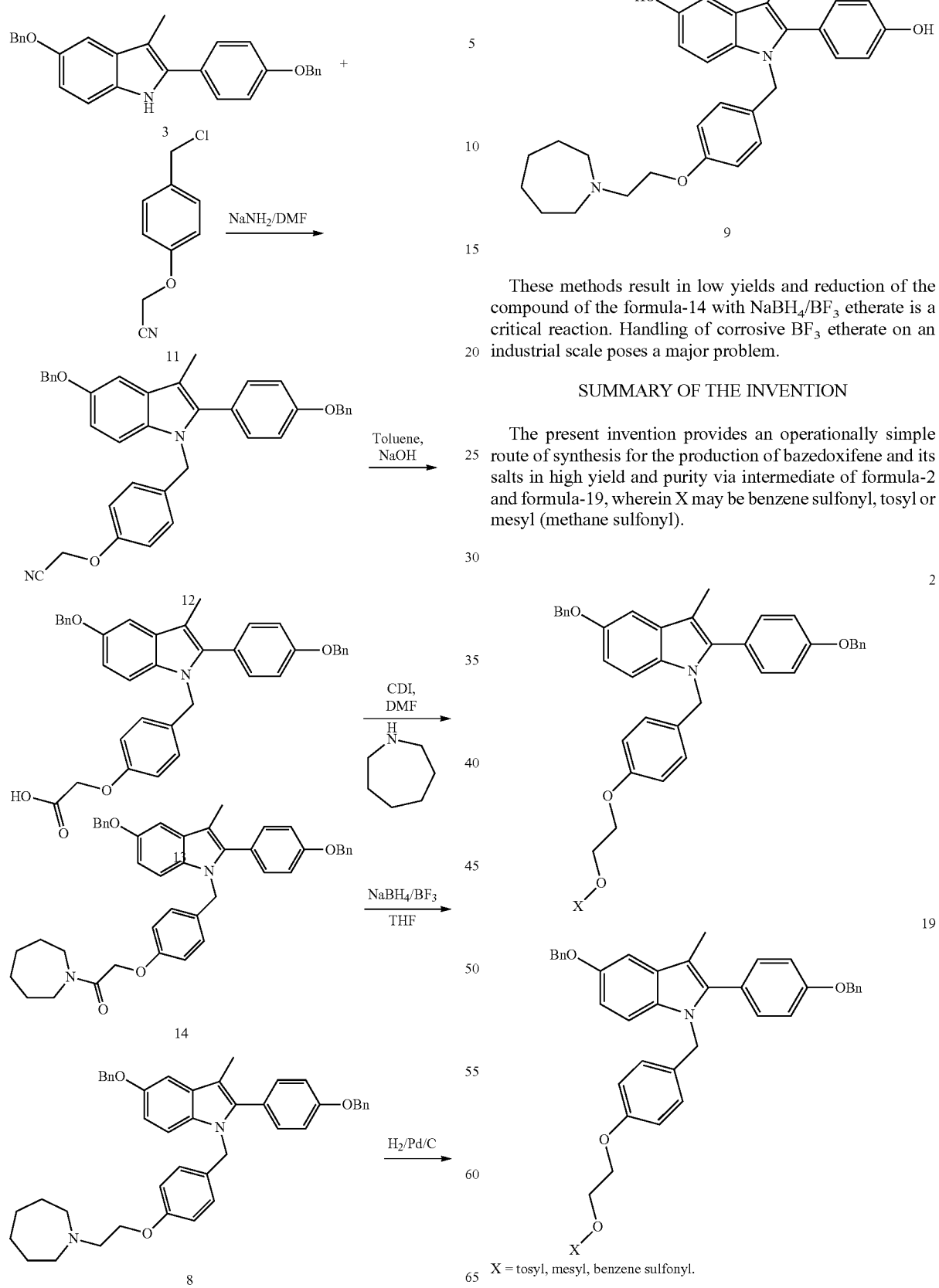

These methods result in low yields and reduction of the compound of the formula-14 with NaBH$_4$/BF$_3$ etherate is a critical reaction. Handling of corrosive BF$_3$ etherate on an industrial scale poses a major problem.

SUMMARY OF THE INVENTION

The present invention provides an operationally simple route of synthesis for the production of bazedoxifene and its salts in high yield and purity via intermediate of formula-2 and formula-19, wherein X may be benzene sulfonyl, tosyl or mesyl (methane sulfonyl).

The scheme-4 below provides two alternatives of converting the intermediate 2 to bazedoxifene with equal advantage.

The present invention also provides a convenient method of preparing the intermediate of formula-2, which can also be used as an intermediate in the production of other close analogs of bazedoxifene. Compound of the formula-3 is condensed with the compound of the formula-18 to provide the key intermediate of the formula-2 as shown in scheme-4 below.

Scheme-4:

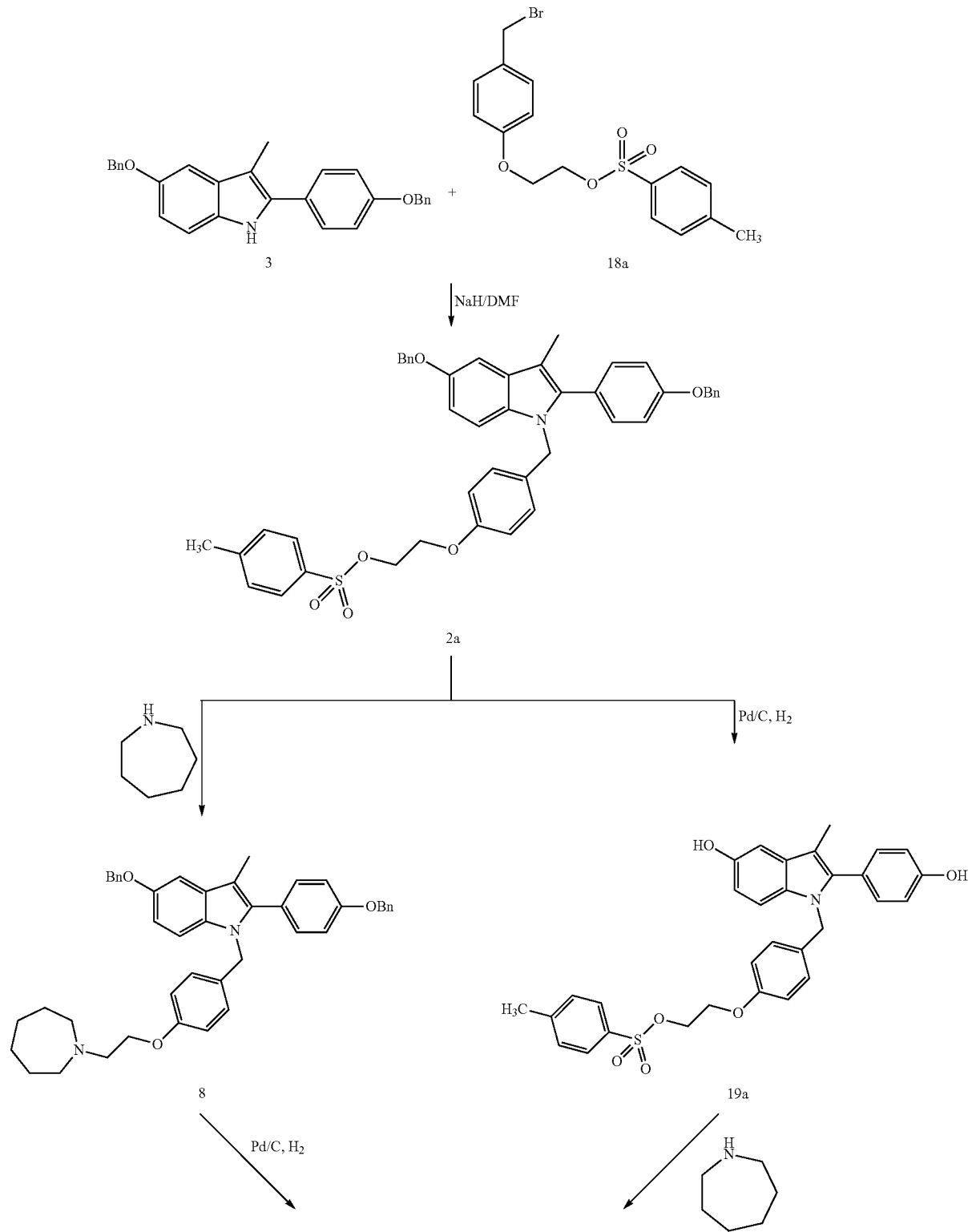

-continued

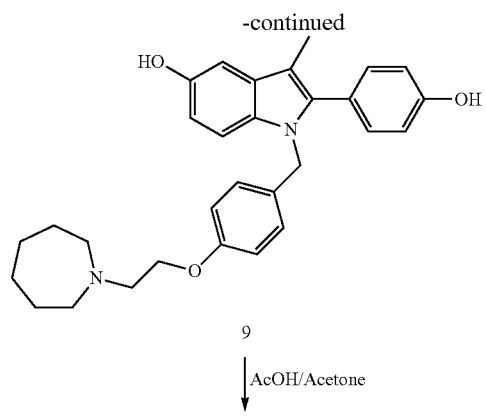

9

↓ AcOH/Acetone

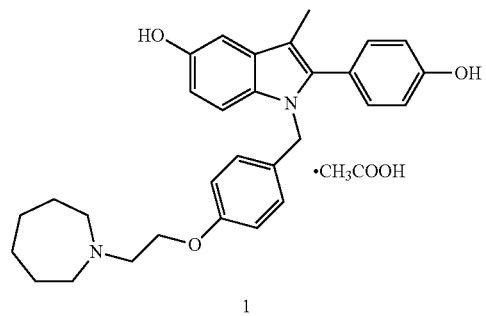

1

DETAILED DESCRIPTION OF THE INVENTION

We have surprisingly found that N-alkylation of the compound of the formula-3 above using the compound of formula-18 leads to pure compound of formula-2a which helps in overcoming the difficulties of the prior art. The intermediate 18 was subsequently converted to bazedoxifene of formula-9 either via compound of formula-8 or via compound of formula-19 in high yield and purity, free from the impurity 3-(4-(2-(azepan-1-yl)ethoxy)benzyl)-2-(4-hydroxy phenyl)-3-methyl-3H-indol-5-ol of formula-22 and impurity 3-(4-(2-(azepan-1-yl)ethoxy)benzyl)-5-(benzyloxy)-2-(4-benzyloxy phenyl)-3-methyl-3H-indo of formula-23.

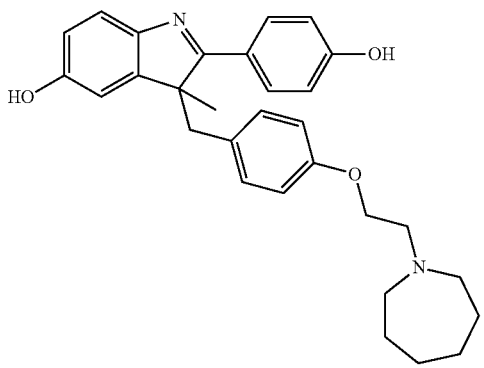

22

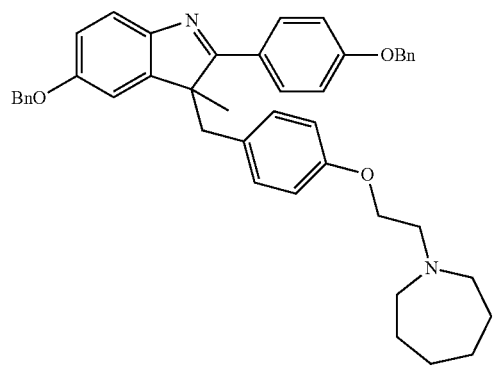

23

According to one aspect of the present invention, the process for the synthesis of bazedoxifene acetate substantially free from impurities of the formulas-22 and 23, comprises the following steps:

a) 5-Benzyloxy-2-(4-benzyloxy phenyl)-3-methyl-1H-indole (formula-3) is reacted with 2-(4-(bromomethyl)phenoxy)ethyl-4-methylbenzenesulfonate of formula-18 in the presence of a suitable base and in a suitable solvent to afford a 2-(4-{[5-(benzyloxy)-2-[4-(benzyloxy)phenyl]-3-methyl-1H-indol-1-yl]methyl}phenoxy)ethyl-4-methylbenzenzene-1-sulfonate of formula-2a.

Suitable bases for this step are inorganic bases such as alkali metal hydrides, alkali metal hydroxides, alkali amides, alkoxides and carbonates. A preferred example of a suitable base is sodium hydride.

Suitable solvents for this step are aromatic hydrocarbons such as toluene and xylene, polar aprotic solvents such as dimethyl sulfoxide, N,N-dimethyl formamide, N,N-dimethyl acetamide, acetonitrile, ethers such as tetrahydrofuran, methyl tetrahydrofuran and mixtures there of. A preferred example of suitable solvent is N,N-dimethyl formamide.

Suitable temperatures for conducting this step are −10° to 30° C., and preferably −10° to 5° C.

For crystallization and purification of the obtained compound of the formula-2a, a suitable solvent may be selected from alcohols, esters or mixtures thereof, preferably methanol and ethyl acetate. This step of purification helps to eliminate the process-related C-alkylated impurity of formula-24.

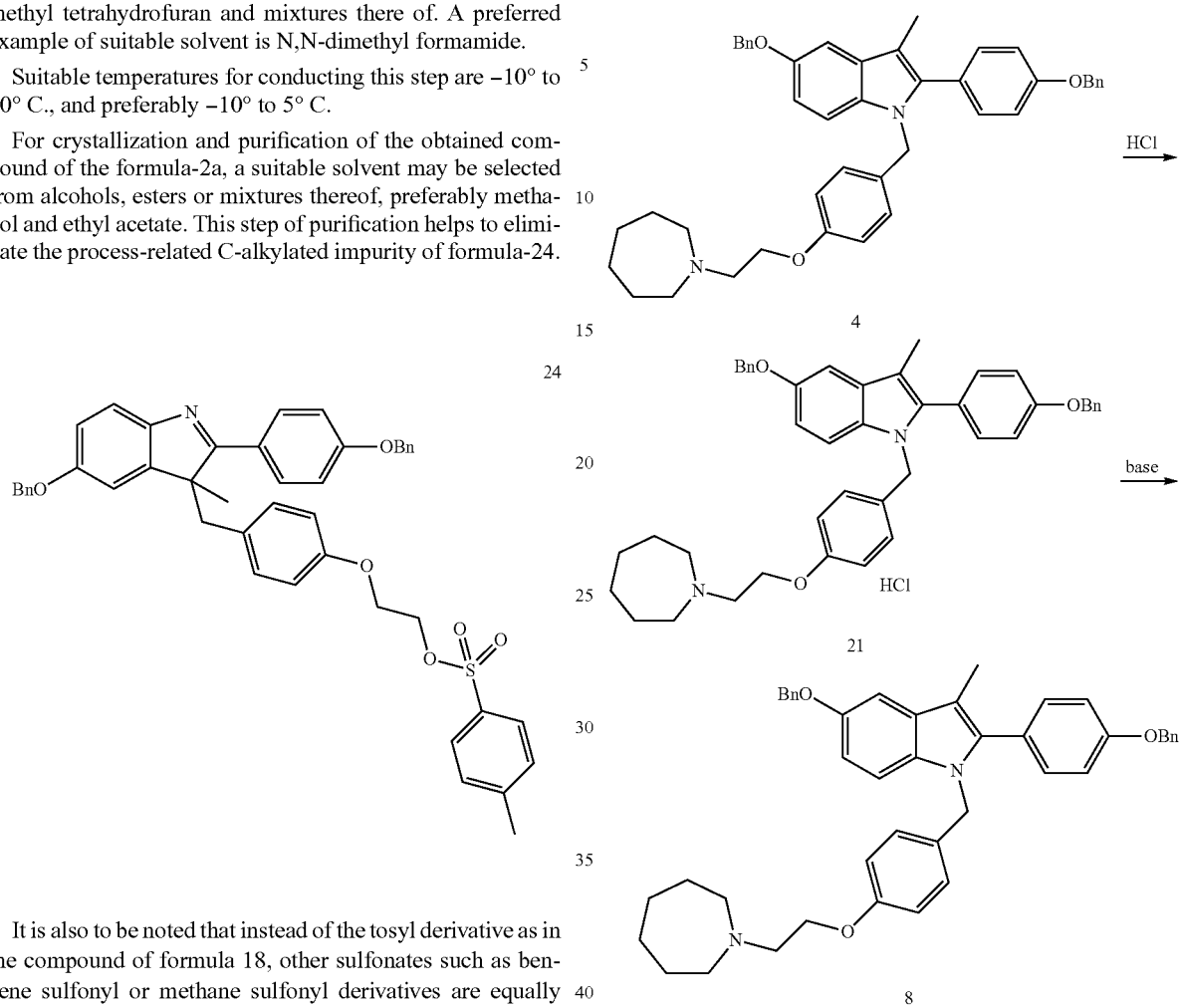

It is also to be noted that instead of the tosyl derivative as in the compound of formula 18, other sulfonates such as benzene sulfonyl or methane sulfonyl derivatives are equally effective.

b) The compound of formula-2a is reacted with hexamethyleneimine in a suitable solvent to afford 5-benzyloxy-2-(4-benzyloxy-phenyl)-3-methyl-1-[4-(2-azepan-1-yl-ethoxy) benzyl]-1H-indole of the formula-8.

The reaction is carried out in a solvent such as an aromatic hydrocarbon like benzene, toluene and xylene or an ether like tetrahydrofuran and methyl tetrahydrofuran, preferably toluene at a temperature between 30° and 90° C., and preferably at 75° C.

The compound of formula-8 is purified by formation of hydrochloride salt in a suitable solvent such as toluene or methyl-tert-butyl ether, preferably toluene with HCl gas or hydrochloric acid at a temperature between 30° and 90° C., preferably at 70° C.

The pure compound of formula-8 is obtained by neutralizing the salt with an inorganic base such as sodium hydroxide or potassium hydroxide in a suitable solvent such as toluene or methyl-tert-butyl ether, preferably toluene at a temperature between 30° to 90° C., preferably at 70° C. This step improves the purity to >99.8% by eliminating the process-related impurities. The high purity of the compound of formula-8 facilitates high purity of bazedoxifene without the need for further purification.

c) Deprotection of the compound of formula-8 under catalytic hydrogenation in a suitable solvent gives bazedoxifene free base of the formula-9.

The reaction is carried out in a suitable solvent such as alcohols, e.g., methanol or ethanol, or a polar aprotic solvent such as ethyl acetate or mixtures thereof, preferably, ethyl acetate at a temperature between 30° to 50° C., preferably at 40° C.

A suitable catalyst for deprotection is palladium on carbon.

The preferred salt bazedoxifene acetate is obtained as known in the prior art by treatment of bazedoxifene free base of formula-9 with acetic acid in a suitable solvent such as ketone solvents, alcohols or ester solvents, preferably ketone solvents, more preferably acetone. The reaction is carried out at a temperature range from room temperature to the reflux temperature of the solvent used.

Another aspect of the present invention is to provide an improved process for the preparation of bazedoxifene acetate of the compound of the formula-1, which comprises of the following steps:

a) This is carried out substantially as described above to obtain pure compound of formula-2a.

b) Deprotection of the compound 2a in a suitable solvent selected from alcohols, esters or ethers, preferably ester solvents like ethyl acetate and a catalyst, preferably palladium on carbon at a temperature of about 30° to 60° C., preferably at 45° C., to give the compound of formula-19.

c) Reacting the compound of formula-19 with hexamethyleneimine in a suitable solvent selected from aromatic hydrocarbons like benzene, toluene or xylene, preferably toluene, at a temperature of about 30° to 75° C., preferably at about 75° C. to give the bazedoxifene free base of formula-9.

The bazedoxifene free base is then converted to the preferred acetate salt with acetic acid in a suitable solvent as described above.

In another embodiment of the present invention, a process for preparing 2-(4-(bromomethyl)phenoxy)ethyl-4-methyl-benzenesulfonate is provided. Preparation of this novel intermediate comprises the following steps (see Scheme-6 below):

a) Reacting 4-hydroxy benzaldehyde with 2-chloro ethanol in the presence of a base like sodium hydroxide or potassium hydroxide preferably sodium hydroxide in a polar solvent like water at a temperature 35° to 105° C., preferably at a temperature of 100 to 105° C., to give the compound of formula-15.

b) Reacting the compound of formula-15 with p-toluene sulfonyl chloride in the presence of a suitable organic base such as pyridine, triethylamine or N,N-dimethyl amino pyridine, preferably triethylamine in a suitable solvent such as dichloro methane or ethylene dichloride at a temperature of about 25° to 30° C. affords the compound of formula-16.

It is also to be noted that instead of p-tosyl chloride, other sulfonyl chlorides such as methane sulfonyl chloride or benzene sulfonyl chloride may be used which work equally well giving the corresponding sulfonates.

c) Reducing the compound of formula-16 obtained with metal hydrides such as sodium borohydride or lithium aluminium hydride in a suitable solvent selected from alcohols like methanol, ethanol or 2-propanol at a temperature of about 0° to 35° C., preferably at a temperature of about 0° to 5° C., gives the compound of the formula-17.

d) Brominating the compound of formula-17 with a suitable brominating agent such as hydrobromic acid, thionyl bromide or phosphorous tribromide, in a suitable solvent like dichloromethane or ethylene dichloride at a temperature of about 0° to 40° C., preferably 25° to 30° C., affords the compound of the formula-18.

Scheme-6:

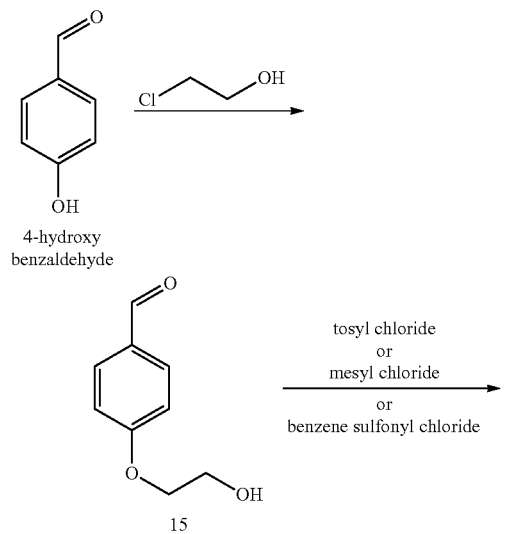

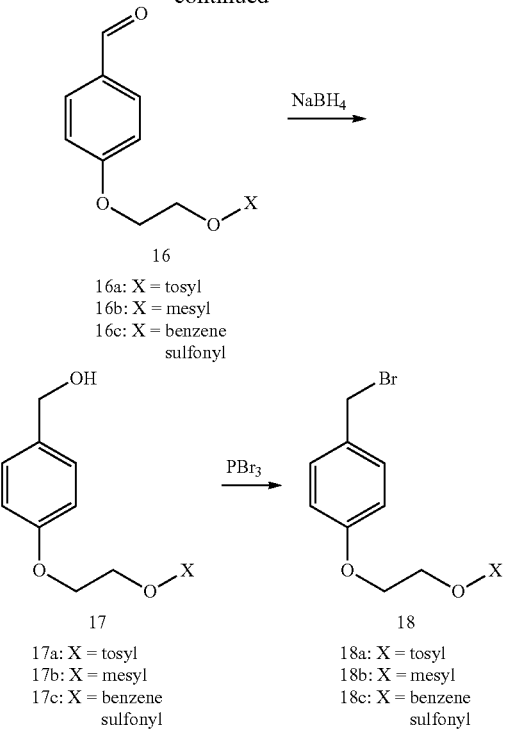

The processes described above are illustrated in the examples below. The examples do not limit the scope of the invention in any way. A person skilled in the art would be able to modify the details to achieve the objectives of the present invention.

Example 1

Preparation of 2-(4-formyl phenoxy)ethyl-4-methyl benzene sulfonate (formula-16a)

A solution of tosyl chloride (68.9 g, 361 mmol) in 500 ml dichloro methane was added drop wise with stirring to a solution of 4-(2-hydroxyethyloxy)benzaldehyde of formula-15 (50 g, 301 mmol) (*J. Am. Chem. Soc.,* 1951, 73(3), pp 906-912) in 250 ml of dichloro methane at ambient temperature followed by addition of 63 ml (451 mmol) of triethylamine to the reaction mixture and stirred for 12 hrs. Water (300 ml) was added to reaction mixture and the layers separated. The dichloromethane layer was washed with water (250 ml) and then brine (200 ml), dried with $MgSO_4$ and evaporated to give a crude product. This was suspended in methyl-tert-butyl ether (150 ml) and stirred for 30 min, filtered, washed with MTBE (50 ml) and dried under vacuum to give the title compound. Yield: 82 g (85%) M.R: 102°-105° C.

$H^1$-NMR ($CDCl_3$): δ 9.88 (s, 1H); 7.82 (d, 2H); 7.79 (d, 2H); 7.33 (d, 2H); 6.88 (d, 2H); 4.39 (t, 2H); 4.22 (t, 2H); 2.45 (s, 3H)

Example 2

Preparation of 2-(4-formyl phenoxy)ethyl methane sulfonate (formula-16b)

The title compound was prepared analogous to example 1 above using methane sulfonyl chloride used in place of tosyl chloride. M.R: 67°-69° C.

H$^1$-NMR (CDCl$_3$): δ 9.90 (s, 1H); 7.84 (d, 2H); 7.01 (d, 2H); 4.59 (t, 2H); 4.32 (t, 2H); 3.1 (s, 3H)

Example 3

Preparation of 2-(4-formyl phenoxy)ethyl benzene sulfonate (formula-16c)

The title compound was prepared analogous to example 1 above using benzene sulfonyl chloride used in place of tosyl chloride. M.R: 92°-94° C.

H$^1$-NMR (CDCl$_3$): δ 9.88 (s, 1H); 7.96-7.92 (m, 2H); 7.83-7.78 (m, 2H); 7.77-7.65 (tt, 1H); 7.59-7.55 (m, 2H); 6.87 (d, 2H); 4.42 (t, 2H); 4.23 (t, 2H)

Example 4

Preparation of 2-(4-hydroxymethyl)phenoxy)ethyl-4-methyl benzene sulfonate (formula-17a)

To a solution of compound 16a (75 g, 234 mmol), 13.3 g (351 mmol) of sodium borohydride was added in 600 ml of methanol at 0°-5° C. The reaction mixture was stirred for 15 min at 0°-5° C. and for another hour at ambient temperature. Then the reaction mixture was quenched with acetic acid and concentrated under vacuum until no solvent distilled. The gummy residue was partitioned between ethyl acetate (250 ml) and water (250 ml). The layers were separated and the aqueous layer was extracted with ethyl acetate (150 ml). The combined organic layer was washed with water (200 ml) and then brine (200 ml), dried with MgSO$_4$ and concentrated under vacuum to give crude product. The crude product was stirred with 200 ml of heptanes at room temperature for 30 min, filtered, the crystalline material washed with heptanes (50 ml) and dried under vacuum to afford the title compound as a white solid.

Yield: 67.9 g (90%) M.R: 84°-88° C.

H$^1$-NMR (CDCl$_3$): δ 7.83 (d, 2H); 7.36 (d, 2H); 7.27 (d, 2H); 6.90 (d, 2H); 4.61 (s, 2H) 4.38 (t, 2H); 4.16 (t, 2H); 2.45 (s, 3H)

Example 5

Preparation of 2-(4-hydroxymethyl)phenoxy)ethyl methane sulfonate (formula-17b)

This compound was prepared analogous to example 4 above using the starting material obtained from example 2 above. M.R: 85°-88° C.

H$^1$-NMR (CDCl$_3$): 7.29 (d, 2H); 6.88 (d, 2H); 4.62 (d, 2H); 4.56 (t, 2H); 4.23 (t, 2H); 3.09 (s, 3H) 1.67 (s, 1H)

Example 6

Preparation of 2-(4-hydroxymethyl)phenoxy)ethyl benzene sulfonate (formula-17c)

This compound was prepared analogous to example 4 above using the starting material obtained from example 3 above. M.R: 61°-63° C.

H$^1$-NMR (CDCl$_3$): 7.92 (d, 2H); 7.69-7.64 (tt, 1H); 7.58-7.53 (m, 2H); 7.21 (d, 2H); 6.74 (d, 2H); 4.60 (s, 2H); 4.37 (t, 2H); 4.13 (t, 2H); 1.63 (s, 1H)

Example 7

Preparation of 2-(4-bromomethyl)phenoxy ethyl-4-methyl benzene sulfonate (formula-18a)

To a solution of compound 17a (50 g, 155 mmol) from example 4 in 500 ml dichloromethane 31.5 g (116 mmol) of phosphorus tribromide was added drop wise at 0-5° C. The reaction mixture was stirred for 4 to 5 hrs at ambient temperature. The reaction mixture was decomposed in chilled water and the layers separated. The dichloromethane layer was washed with saturated sodium bicarbonate solution (250 ml), water (150 ml) and brine (150 ml) successively. The organic layer was dried over MgSO$_4$ and evaporated to give crude product. The residual solid was suspended in 125 ml of heptanes and stirred for 30 min, filtered, washed with 50 ml heptanes and dried under vacuum to afford the title compound as a white solid.

Yield: 53.7 g (90%); M.R: 79°-83° C.

H$^1$-NMR (CDCl$_3$): δ 7.79 (d, 2H); 7.32 (d, 2H); 7.26 (d, 2H); 6.72 (d, 2H); 4.47 (s, 2H); 4.34 (t, 2H); 4.13 (t, 2H); 2.45 (s, 3H)

Example 8

Preparation of 2-(4-bromomethyl)phenoxy ethyl methane sulfonate (formula-18b)

This compound was prepared analogous to example 7 above using the starting material obtained from example 5 above.

M.R: 74°-76° C.

H$^1$-NMR (CDCl$_3$): δ 7.32 (d, 2H); 6.85 (d, 2H); 4.55 (t, 2H); 4.49 (s, 2H), 4.23 (t, 2H); 3.08 (s, 3H)

Example 9

Preparation of 2-(4-bromomethyl)phenoxy ethyl benzene sulfonate (formula-18c)

This compound was prepared analogous to example 7 above using the starting material obtained from example 6 above.

M.R: 112°-114° C.

H$^1$-NMR (CDCl$_3$): δ 7.95-7.92 (m, 2H); 7.66-7.64 (tt, 1H); 7.58-7.53 (m, 2H); 7.26 (d, 2H); 6.72 (d, 2H), 4.47 (s, 2H); 4.38 (t, 2H); 4.13 (t, 2H)

Example 10

Preparation of 2-(4-{[5-(benzyloxy)-2-[4-(benzyloxy)phenyl]-3-methyl-1H-indol-1-yl]methyl}phenoxy)ethyl-4-methylbenzenzene-1-sulfonate (formula 2a)

A solution of 5-benzyloxy-2-(4-benzyloxyphenyl)-3-methyl-1H-indole of formula 3 (25 g, 59.6 mmol) in dimethyl formamide (DMF, 100 ml) was cooled to −10° to −5° C. and treated with sodium hydride (4.8 g, 120 mmol). Reaction mixture was stirred for 30 min and then 2-(4-bromomethyl) phenoxy ethyl-4-methyl benzene sulfonate of formula 18a (27.5 g, 71.5 mmol) in DMF (100 ml) was added and stirred for 3 hrs at −5° to 0° C. The reaction mixture was quenched with acetic acid, poured into water (200 ml) and extracted with dichloromethane (2×200 ml). The dichloromethane layer was separated and washed with water (200 ml) and brine (100 ml), dried over MgSO$_4$ and concentrated under vacuum to afford the crude material. This was found to contain 25-30% of C-alkyl impurity of formula-24. The crude material was dissolved in 150 ml of methanol-ethyl acetate mixture (5:2) at 50° C. and stirred for 30 min at ambient temperature. A white precipitate fell out of solution almost immediately. The precipitate was filtered, washed with 50 ml methanol and dried under vacuum to give 25.8 g (60%) of 2a as a white solid. M.R: 147-149° C. Purity by HPLC: 98% (Area)

H$^1$-NMR (CDCl$_3$): δ 7.77 (d, 2H); 7.50-7.29 (m, 12H); 7.20 (d, 2H); 7.13 (d, 1H); 7.06-6.93 (m, 3H); 6.89 (dd, 1H); 6.80 (d, 2H); 6.61 (d, 2H); 5.13 (s, 2H); 5.09 (s, 4H); 4.30 (t, 2H); 4.05 (t, 2H); 2.41 (s, 3H), 2.24 (s, 3H)

The C-alkyl impurity of formula-24 was isolated by column chromatography using silica gel from mother liquors.

H$^1$ NMR (CDCl$_3$): δ 8.09 (d, 2H); 7.74 (d, 2H); 7.49-7.25 (m, 13H); 7.07 (d, 2H); 6.88 (d, 2H); 6.37 (d, 2H); 6.29 (d, 2H); 5.15 (s, 2H); 5.10 (s, 2H); 4.23 (t, 2H); 3.94 (t, 2H): 3.37 (q, 2H); 2.42 (s, 3H); 1.66 (s, 3H)

Example 11

Preparation of 2-(4-{[5-(benzyloxy)-2-[4-(benzyloxy)phenyl]-3-methyl-1H-indol-1-yl]methyl}phenoxy)ethyl methane sulfonate (formula 2b)

This compound was prepared analogous to example 10 using 2-(4-bromomethyl)phenoxy ethyl methane sulfonate from example 8 in place of 2-(4-bromomethyl)phenoxy ethyl-4-methyl benzene sulfonate. M.R: 126°-128° C.

H$^1$-NMR (CDCl$_3$): δ 7.4-7.31 (m, 12H); 7.20 (d, 2H); 7.13 (d, 1H); 7.06-6.99 (m, 3H); 6.87 (dd, 1H); 6.85 (d, 2H); 6.72 (d, 2H); 5.13 (s, 2H); 5.12 (s, 2H); 5.09 (s, 2H); 4.51 (t, 2H); 4.15 (t, 2H); 3.05 (s, 3H); 2.24 (s, 3H)

Example 12

Preparation of 2-(4-{[5-(benzyloxy)-2-[4-(benzyloxy)phenyl]-3-methyl-1H-indol-1-yl]methyl}phenoxy)ethyl benzene sulfonate (formula 2c)

This compound was prepared analogous to example 10 using 2-(4-bromomethyl)phenoxy ethyl benzene sulfonate from example 9 in place of 2-(4-bromomethyl)phenoxy ethyl-4-methyl benzene sulfonate. M.R: 105°-108° C.

H$^1$-NMR (CDCl$_3$): δ 7.93-7.89 (m, 2H); 7.62-7.59 (tt, 1H); 7.54-7.31 (m, 12H); 7.23 (d, 2H); 7.14 (d, 1H); 7.06-6.99 (m, 3H); 6.86 (dd, 1H); 6.80 (d, 2H); 6.60 (d, 2H); 5.13 (s, 2H); 5.09 (s, 4H); 4.33 (t, 2H); 4.06 (t, 2H); 2.24 (s, 3H)

Example 13

Preparation of 5-Benzyloxy-2-(4-benzyloxy-phenyl)-3-methyl-1-[4-(2-azepan-1-yl-ethoxy)benzyl]-1H-indole (formula-8)

A solution of compound 2a from example 10 (18 g, 24.8 mmol) in toluene (180 ml) was treated with hexamethylene-imine (12.3 g, 124.3 mmol) and heated to 70-75° C. for 12 hrs. The reaction mixture was concentrated and taken up in fresh toluene (100 ml). Toluene layer was washed with water (100 ml) and brine (100 ml), dried (MgSO$_4$) and concentrated under vacuum to afford a crude material. This was suspended in methanol (100 ml), stirred for 1 hr at ambient temperature, filtered, washed with methanol (50 ml) and dried to get 15.3 g (95%) of title compound. HPLC: 96%

Example 14

Preparation of 5-Benzyloxy-2-(4-benzyloxy-phenyl)-3-methyl-1-[4-(2-azepan-1-yl-ethoxy)benzyl]-1H-indole (formula-8)

Compound was prepared by procedure as in example 12 using starting material 2b in place of 2a.

Example 15

Preparation of 5-Benzyloxy-2-(4-benzyloxy-phenyl)-3-methyl-1-[4-(2-azepan-1-yl-ethoxy)benzyl]-1H-indole (formula-8)

Compound was prepared by procedure as in example 12 using starting material 2c in place of 2a.

Example 16

Purification of Formula-8 via Hydrochloride Salt (Formula-21) Formation

The compound 5-Benzyloxy-2-(4-benzyloxy-phenyl)-3-methyl-1-[4-(2-azepan-1-yl-ethoxy)benzyl]-1H-indole from example 13 (14.5 g, 22.2 mmol) was dissolved in 145 ml toluene and heated to 65-70° C. Hydrochloric acid (5.6 ml, 55.5 mmol) was added during 10 to 15 min at 65-70° C. Reaction mixture was stirred for 30 min at 65-70° C. and for 30 min at 30-35° C., filtered, washed the compound with toluene (50 ml) and dried under vacuum to get 14.5 g hydrochloride salt.

The hydrochloride salt (14.5 g) was suspended in toluene (145 ml) at ambient temperature and stirred for 10 min. A solution of sodium hydroxide (3.5 g) in water (75 ml) was added to the reaction mixture during 10 to 15 min. Then the reaction mixture was heated to 65-70° C. and stirred for 1.5 hrs. After cooling the reaction mixture to ambient temperature the organic layer was separated. Aqueous layer was extracted with toluene (50 ml). The combined organic layer was washed with water (100 ml), dried (MgSO$_4$) and treated with activated charcoal for 30 to 45 min at 70-75° C. Charcoal was filtered through celite bed and clear filtrate was concentrated to get a solid material, which was suspended in methanol (75 ml) and stirred for 30 min at ambient temperature, filtered, washed with methanol (25 ml) and dried under vacuum to afford pure compound 8 (13.0 g, 90%)

M.R: 109-111° C.; HPLC: 99.9%

Example 17

Preparation of Bazedoxifene Free Base (Formula-9)

The compound 8 from example 14 (17 g, 26 mmol) was dissolved in 340 ml of ethyl acetate and was subjected to catalytic hydrogenation with 5.1 g of 10% Pd/C, 50% wet, at a pressure of 4 to 5 kg/cm² at 30-35° C. until completion of the reaction (6-7 hrs) as verified by TLC. The mixture was filtered and washed with ethyl acetate (50 ml). The filtrate was distilled completely under vacuum to afford a white foamy solid. Heptane (100 ml) was added to the solid and stirred for 30 min, filtered, washed with heptane (25 ml) and dried under vacuum to get title compound 9 (11.9 g, 97%) M.R: 170-174° C.; HPLC: 99.8% with the C-alkylated impurity below detection limits.

Example 18

Preparation of 2-(4-((5-hydroxy-2-(4-hydroxy phenyl)-3-methyl-1H-indol-1-yl)methyl)phenoxy ethyl-4-methyl benzene sulfonate (formula-19)

Compound 2a from example 10 (17 g, 23.5 mmol) dissolved in 340 ml of ethyl acetate was subjected to catalytic hydrogenation as in example 15 above to get title compound-19 (10.9 g, 85%)

H¹ NMR (CDCl₃): δ 7.7 (d, 2H); 7.28 (d, 2H); 7.12 (d, 2H); 7.0-6.90 (m, 2H); 6.84 (d, 2H); 6.78 (d, 2H); 6.72 (dd, 1H); 6.59 (d, 2H); 5.07 (s, 2H); 4.29 (t, 2H); 4.04 (t, 2H); 2.4 (s, 3H); 2.19 (s, 3H)

Example 19

Preparation of Bazedoxifene Free Base (Formula-9) from Compound 19

A solution of compound 19 from example 18 (10 g, 18.4 mmol) in toluene (100 ml) was treated with hexamethyleneimine (9.1 g, 92 mmol) and heated to 70-75° C. for 12 hrs. Then the reaction mixture was concentrated and taken up in fresh toluene (100 ml). Toluene layer was washed with water (100 ml) and brine (100 ml), dried (MgSO₄) and concentrated to obtain a foamy solid (8.1 g, 94%). The crude material was purified by column chromatography using silica gel to get 6.9 g (80%) of the title compound. M.R: 170-174° C.; HPLC: 99.8% with the C-alkylated impurity below detection limits.

Example 20

Preparation of Bazedoxifene Acetate (Formula-1)

Bazedoxifene free base from example 17 or from example 19 (10 g, 21.2 mmol) was suspended in acetone (80 ml) and heated to 50-55° C. After getting a clear solution, a mixture of acetic acid (1.4 g, 23.3 mmol) and acetone (10 ml) was added slowly. Then the reaction mixture was allowed to cool at 20-25° C., stirred for 2 hrs, filtered the product formed, washed with acetone (20 ml) and dried under vacuum to afford the title compound in high yield and high purity (12.7 g, 95%) M.R: 176-181° C. HPLC: 99.9%.

We claim:

1. A process for preparation of 1-{4-[2-(azepan-1-yl)ethoxy]benzyl}-2-(4-hydroxyphenyl)-3-methyl-1H-indol-5-ol (formula 9, also known as bazedoxifene) and its acetate salt, comprising the steps of:

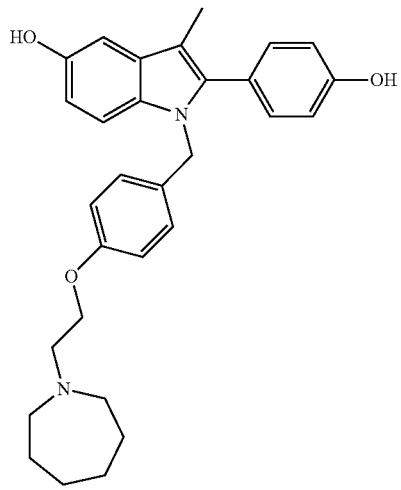

9

(a) reacting 5-benzyloxy-2-(4-benzyloxyphenyl)-3-methyl-1H-indole (formula 3) with the ester of a sulphonic acid of 2-(4-bromomethyl)phenoxyethanol (formula 18) in the presence of sodium hydride in a solvent at a temperature between −10° and 10° C. until completion of the reaction,

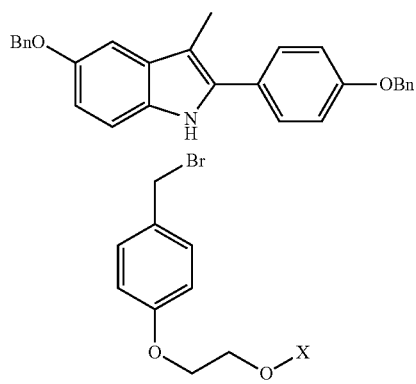

X = tosyl, mesyl, benzene sulfonyl, (b) quenching the reaction mixture with acetic acid and water, followed by extraction with dichloromethane, isolating the crude product, crystallising it from a suitable polar solvent to obtain a pure ester of the sulphonic acid of 2-(4-{[5-(benzyloxy)-2-[4-(benzyloxy)phenyl]-3-methyl-1H-indol-1-yl]methyl}phenoxy)ethanol (formula 2),

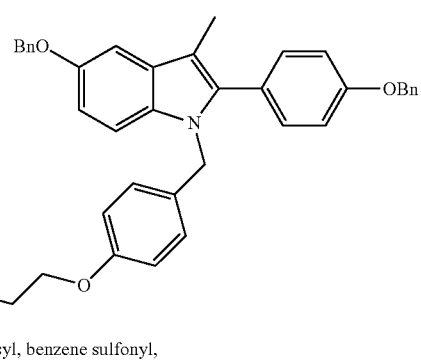

X = tosyl, mesyl, benzene sulfonyl, (c) treating the ester so obtained (formula 2) with hexamethylenimine in a non-polar solvent at a temperature between 70° and 80° C. and isolating the crude product 1-{4-[2-(azepan-1-yl)ethoxy]benzyl}-5-benzyloxy-2-(4-benzyloxyphenyl)-3-methyl-1H-indole (formula 8), purifying it by forming its hydrochloride salt, crystallizing the pure hydrochloride salt, treating the hydrochloride salt with an inorganic base to liberate pure free base with greater than 99% purity by HPLC, catalytically debenzylating the product (formula 8) in the presence of palladium-carbon to obtain the free base of bazedoxifene (formula 9) having a purity greater than 99.8% by HPLC with a C-alkylated impurity below the detectable limit,

8

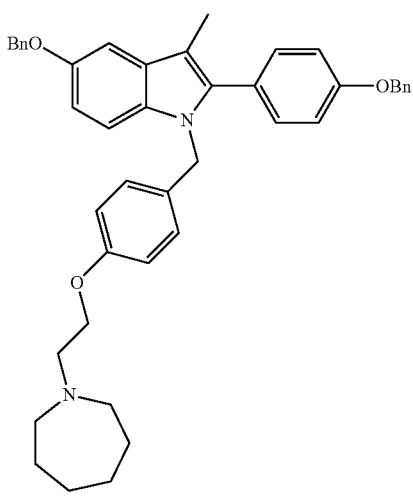

or optionally:
first debenzylating the ester (formula 2) catalytically in the presence of palladium-carbon to obtain the ester of sulphonic acid of 2-{4-[5-hydroxy-2-(4-hydroxyphenyl)-3-methyl-1H-indol-1-yl]methyl}phenoxyethanol (formula 19) followed by reaction with hexamethylenimine in a non-polar solvent at a temperature between 70° and 80° C. and isolating bazedoxifene free base (formula 9)having a purity greater than 99.8% by HPLC with a C-alkylated impurity below the detectable limit, and

19

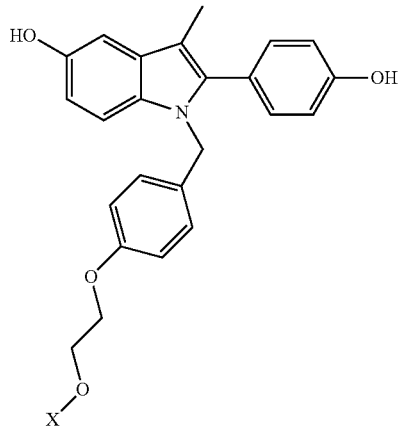

X = tosyl, mesyl, benzene sulfonyl, (d) optionally converting the free bazedoxifene base to its acetate salt by reaction with acetic acid.

2. A process according to claim 1, step a, wherein sulfonic acid is selected from the group 4-methyl benzene sulfonic acid, benzene sulfonic acid and methane sulfonic acid.

3. A process according to claim 1, step a, wherein the solvent is selected from the group consisting of toluene, xylene, dimethyl sulfoxide, N,N-dimethyl formamide and acetonitrile.

4. A process according to claim 1, step b, wherein the polar solvent is either ethyl acetate or methanol or a mixture thereof.

5. A process according to claim 1, step c, wherein the non-polar solvent is selected from the group consisting of toluene, xylene, tetrahydrofuran and methyl tetrahydrofuran or mixtures thereof.

* * * * *